United States Patent [19]

Bennish

[11] Patent Number: 4,457,315
[45] Date of Patent: Jul. 3, 1984

[54] CARDIAC ARRHYTHMIA DETECTION AND RECORDING

[76] Inventor: Arvin Bennish, 5615 Wing Lake Rd., Birmingham, Mich. 48010

[21] Appl. No.: 87,590

[22] Filed: Oct. 22, 1979

Related U.S. Application Data

[63] Continuation-in-part of Ser. No. 943,204, Sep. 18, 1978, abandoned.

[51] Int. Cl.³ .............................................. A61B 5/04
[52] U.S. Cl. ...................................... 128/704; 128/711
[58] Field of Search .................. 346/33 ME; 128/702, 128/703, 704, 706, 708, 710, 711

[56] References Cited

U.S. PATENT DOCUMENTS

| | | | |
|---|---|---|---|
| 3,524,442 | 8/1970 | Horth | 128/703 |
| 3,759,248 | 9/1973 | Valiquette | 128/703 |
| 3,799,148 | 3/1974 | Rowen | 128/711 |
| 3,824,990 | 7/1974 | Baule | 128/702 |
| 3,874,370 | 4/1975 | Harris et al. | 128/711 |
| 3,934,267 | 1/1976 | Kosaka et al. | 128/711 |
| 4,183,354 | 1/1980 | Sibley et al. | 128/711 |

Primary Examiner—William E. Kamm
Attorney, Agent, or Firm—Barnes, Kisselle, Raisch, Choate, Whittemore & Hulbert

[57] ABSTRACT

Cardiac arrhythmias are detected by measuring the duration of the first derivative of the QRS component signal of a cardiac rhythm and comparing such duration to a running average duration, and/or by measuring the duration of the R-R interval and comparing such interval to a running average interval. A cassette recorder in a portable battery-operated monitor for ambulatory patients is activated in response to an arrhythmia detected by either one of the above techniques. The cardiac rhythm signal is fed to the recorder through a delay network such that the recorded signal brackets the detected arrhythmia. A manual record switch is also provided for separate wearer actuation to record what he considers to be unusual heart activity.

7 Claims, 11 Drawing Figures

CARDIAC ARRHYTHMIA DETECTION AND RECORDING

This is a continuation-in-part of application Ser. No. 943,204 filed Sept. 18, 1978 and now abandoned.

The present invention is directed to monitoring and recording apparatus and methods and, more particularly, to a method and apparatus for monitoring the heart activity of a cardiac patient, detecting cardiac arrhythmias and recording such arrhythmias in real time for later analysis. Yet more specifically, the invention is directed to portable battery-operated monitors for detecting and recording arrhythmia in ambulatory cardiac patients.

Cardiac monitoring apparatus are illustrated in the following U.S. Pat. Nos.: 3,658,055; 3,759,248; 3,824,990; 3,832,994; 3,858,034; 3,861,387 and 4,023,564. These disclosures are generally directed to sophisticated systems for monitoring and/or diagnosing cardiac arrhythmia in the hospital environment of a cardiac care unit, and are not well suited for portable monitoring of ambulatory patients. Reference may also be had to Kosowsky, "Holter Monitoring", *Journal of Continuing Education in Cardiology*, Vol. 14, No. 2, February 1978, pages 13–21; Jenkins et al, "Computer Diagnosis of Abnormal Cardiac Rhythms Employing a New P-wave Detector for Interval Measurement", *Computers and Biomedical Research*, 1978, pages 17–33; Harrison et al, "Ambulatory Electrocardiography for Diagnosis and Treatment of Cardiac Arrhythmias", *The New England Journal of Medicine*, 1976, pages 373–380; Dreifus et al, "Newer Techniques in Cardiac Monitoring", *Heart and Lung*, July-August 1975, pages 568–572; and Feldman et al, "Computer Detection of Ventricular Ectopic Beats", *Computers and Biomedical Research*, 1971, pages 666–674.

Desirability of providing electronic apparatus for automatically detecting cardiac arrhythmias has heretofore been recognized. Similarly, it has been recognized as desirable to provide combined detection and recording apparatus as a single portable unit which may be worn by a cardiac outpatient to monitor heart activity while the patient follows his daily routine. Such portable apparatus should be compact, rugged and lightweight, battery operated with low power consumption, and yet responsive to a wide variety of cardiac arrhythmia types. Similarly, the apparatus should be responsive to critical arrhythmias indicative of cardiac pathology without being sensitive to extraneous false positives caused by noise or noncardiac muscular activity. The techniques and apparatus proposed in the prior art are not considered to satisfy the above-noted and other desirable, and in some cases critical, features in apparatus of the subject type.

Moreover, some portable apparatus which have achieved some commercial acceptance contemplate continuous recording of heart activity for a specific time duration, such as twenty-four hours. Where the activity is recorded on a magnetic tape cassette, for example, the cassette must be played back and monitored on a CRT by a skilled technician for pathological events. Such a technique is very expensive and does not achieve optimum reliability. Additionally, continuous recording by a magnetic tape cassette recorder, for example, results in substantial power drain with the consequent possibility of power failure. Other prior art apparatus contemplate only manually-activated recording when a wearer thinks that he is experiencing unusual heart activity. It has been demonstrated, however, that persons are likely to recognize about 20% of clinically significant events during waking hours, and even fewer while asleep.

Accordingly, it is a general object of the present invention to provide improved cardiac monitoring apparatus and method which overcomes and satisfies the foregoing problems and difficulties.

More specific objects of the invention are to provide a portable cardiac monitoring apparatus which may be worn by a cardiac outpatient without substantially interfering with his daily routine, which is automatically responsive to a wide variety of cardiac pathological events, which records such events in real time together with preceding and/or subsequent "normal" heart activity for later analysis, which simplifies arrhythmia detection techniques by recording only clinically significant events while minimizing false spurious recording, which significantly improves the effectiveness and efficiency of a battery-operated portable cardiac recorder, which has an enhanced signal-to-noise ratio for reduced sensitivity to extraneous or false positives, and/or which includes provision for manual activation of the recorded by the wearer both for recording what he considers to be unusual heart activity and for recording a "normal" cardiac signal at desired intervals for purposes of comparison.

A further object of the invention is to provide cardiac arrhythmia detection circuitry and method which is particularly well adapted for use in a portable cardiac monitoring apparatus and yet may be used to advantage in a full-scale hospital cardiac care unit.

The present invention, together with additional objects, features and advantages thereof, will be best understood from the following description, the appended claims and the accompanying drawings in which:

Figures 1, 2:
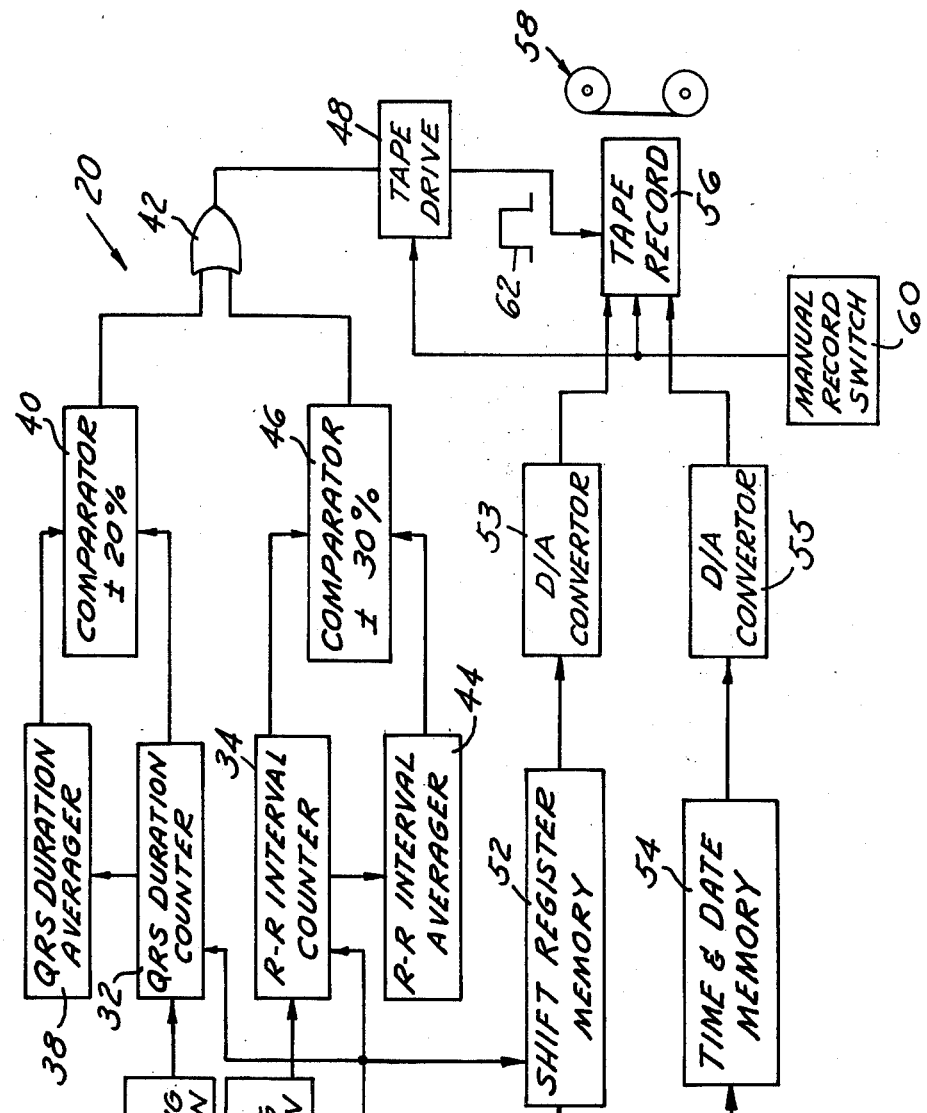
FIG. 1 is a functional block diagram of a presently preferred embodiment of the cardiac arrhythmia detection and recording apparatus provided by the invention.
FIGS. 2–9 are graphical waveforms useful in understanding operation of the invention, FIGS. 3–9 being drawn to scale.

FIG. 1 illustrates a presently preferred embodiment of the detection and recording apparatus 20 provided by the invention as comprising a differential input amplifier 22 connected to conventional cardiac electrodes 24 suitably positioned on a patient 26. The output of amplifier 22 is connected through a high pass filter 28 to the input of a differentiating amplifier 30. The output of differentiating amplifier 30 is connected through respective zero-crossing detection circuits 31,33 to the inputs of a QRS duration counter 32 and an R—R interval counter 34. Counters 32,34 also have a counting input connected to a one-kilohertz clock oscillator 36. One output of counter 32 is connected to a QRS duration average computation circuit 38 which preferably receives and stores a selected number of successive QRS duration signals from counter 32 and computes therefrom a running average QRS duration. In a preferred embodiment of the invention, averager 38 is responsive to the QRS components of the three cardiac rhythm signals immediately preceding the duration signal stored in counter 32. The outputs of averager 38 and counter 32 are connected to a comparator 40 which provides a first signal to an OR gate 42 when the duration indicated in counter 32 is greater or less than the running average duration indicated by averager 38 by an amount equal to or greater than twenty percent of the running average.

Similarly, R—R interval counter 34 is connected to an R—R interval averager 44 for computing a running average R—R interval over a plurality of, preferably three, immediately preceding QRS cardiac rhythm signals. Counter 34 and averager 44 are connected to a comparator 46 which provides a second signal to OR gate 42 when the R—R interval indicated by counter 34 is greater or less than the running average R—R interval indicated by averager 44 by an amount equal to or greater than thirty percent of the average interval. OR gate 42 provides control signal to a tape drive circuit 48 in response to a signal from either comparator 40 or comparator 46, or both.

The output of input amplifier 22 is also connected through an analog-to-digital convertor 50 which provides digital signals in real time to a shift register memory 52 indicative of the amplitude of the cardiac rhythm signal. The gate input of memory 52 is connected to clock oscillator 36. Preferably, memory 52 comprises a 3000-word serial shift register memory which, when combined with a one-kilohertz clock oscillator frequency, provides digital signals at the memory output as a sampled replica of the cardiac rhythm input signals effectively delayed by a period of three seconds. Clock oscillator 36 is also connected to the sampling or gating input of a time and date memory circuit 54. The outputs of memories 52,54 are connected through correspondingly respective digital-to-analog convertors 53,55 to two input channels of a three-channel tape recorder circuit 56 which is responsive to a control signal from tape drive 48 to record the analog signals from convertors 53,55 on two channels of a cassette tape illustrated schematically at 58. A manual record switch 60 which may be activated by the patient 26 has one output connected to a tape drive 48 and a second output connected to a third channel of tape recorder 56.

The output of tape drive 48 is a retriggerable pulsed signal 62 of predetermined duration, preferably on the order of six seconds. Thus, when the tape drive is activated by an control signal from OR gate 42, cardiac rhythm signals are recorded on cassette 58 which effectively bracket the detected pathological event. Stated differently, the delayed output from memory 52 precedes the detected cardiac arrhythmia by approximately three seconds, while the tape drive signal 62 has a duration of about six seconds, so that the recorded rhythm signals includes approximately three seconds preceding and three seconds following the pathological event. Time and date of the detected event indicated by memory 54 are recorded on a second tape channel. When tape drive 48 is activated by manual record switch 60, a six-second cardiac rhythm signal is recorded, together with time and date on the second tape channel and an indication on a third tape channel that the recording was initiated by the manual record switch. If a second arrhythmia is detected during the recording interval, pulsed signal 62 is retriggered and the recording will continue for an additional six seconds. The entire circuit, including the tape drive, is battery operated.

Overall operation of the preferred embodiment of the invention illustrated in FIG. 1 will be evident from the foregoing discussion and need only be outlined briefly in connection with a "typical" electrocardiac rhythm signal of the type illustrated in FIG. 2. The rhythm signal of FIG. 2 includes an atrial P component which has a small positive amplitude, as on the order of 50 to 100 microvolts, and a relatively short duration, as on the order of forty to eighty milliseconds. Thereafter, following a brief interval of quiescence on the order of 150 milliseconds, the signal cycles through a QRS complex corresponding to depolarization of the cardiac muscle in which the signal swings briefly negative in the Q component, then a relatively sharp positive spike of about one millivolt in the R component, and thereafter through a brief negative swing in the S component. A nominal formal QRS duration of 100 milliseconds is typical. After another brief quiescent interval on the order or 200 milliseconds, a slight positive swing corresponding to the T component indicates repolarization of the cardiac muscle. The interval between cardiac rhythm signals is the inverse of the pulse rate and would be one second, for example, for a typical cardiac rhythm at sixty beats per minute.

The frequency cutoff of high pass filter 28 is preferably selected so as to block the low frequency P and T signal components from amplifier 30, the arrhythmia detection circuitry thereby being responsive solely to the QRS rhythm signal components. The input to differential amplifier 30 is set to be responsive to signals above a minimum threshold, and thereby cooperates with filter 28 to block low frequency and/or low voltage high frequency noise signals generated by patient muscular activity. It will be appreciated that the arrhythmia detection circuitry is responsive to the derivative of the input signal via amplifier 30, and is essentially independant of signal amplitude. Thus, filter 28 and amplifier 30 cooperates to overcome problems inherent in prior art techniques which are responsive in whole or in part to the low frequency and low voltage P and T signal components and/or to QRS signal amplitude.

Zero crossing detection circuit 31 is preferably responsive to the "peak" of the first pulse component, i.e. the Q component in FIG. 2 with the P component having been blocked by filter 28 and amplifier 30. QRS duration counter begins counting at this first "peak" and continues counting until the differentiated signal stabalizes at zero, i.e. at the end of the S signal component. Circuit 33 is responsive to the second zero crossing of successive differentiated rhythm signals, i.e. to the peak of the R signal component illustrated in FIG. 2. The QRS duration in counter 32 is compared with the average duration in averager 38 and is thereafter loaded into the averager between QRS rhythm signals for maintaining the running average. The R—R interval counter 34 is responsive to detection circuit 33 sequentially to stop the preceding R—R interval count, compare such count with the running average interval in averager 44, load the preceding count into averager 44 for maintaining a running interval average and then beginning the succeeding R—R interval count. All of such operations are, of course, performed in microseconds and have no practical effect upon the successive R—R interval count.

While arrhythmia monitoring is taking place as described, all of the P, Q, R, S and T components are being continuously sampled and loaded into shift register memory 52 through convertor 50 for later recording if required. When analysis of recorded information is desired, cassette 58 may be taken to a clinic and played back on a tape reader connected to a conventional EKG strip chart recorder. The result will be a series of permanently recorded cardiac rhythm signals exhibiting potential pathological events, each preceded by a corresponding time signal, which may be analyzed by a medical clinician. Thus, the invention both provides for automatic portable recording and eliminates any requirement for scanning of several hours' recording searching for potentially pathological events.

It will be appreciated by persons skilled in the analysis and treatment of cardiovascular disorders that FIG. 2 illustrates a somewhat idealized rhythm signal for a healthy individual. For patients exhibiting some form of cardiac disorder the rhythm signal may vary substantially from that shown in FIG. 2. Indeed, for patients who have suffered permanent heart damage, one or more of the Q, R and S components may be exaggerated or obliterated. Thus, for purposes of the present description and the appended claims, the term "QRS" with reference to rhythm signal components must be read in its broadest aspects as representing the signal which results from the patient's electrical ventricular depolarization. Similarly, the term "R—R interval" signifies the interval between successive rhythm signals, and need not necessarily be measured between identifiable "R" signal components.

In accordance with an important feature of the invention, the arrhythmia detection circuitry, as distinguished from the recording circuitry, is responsive only to the ventricular depolarization or QRS signal and blocks or ignores the atrial depolarization or P component and the ventricular repolarization or T component. (The atrial repolarization signal is masked by the QRS signal and, in any event, is of sufficiently low frequency as to be blocked by filter 28.) An important feature of the present invention lies in recognition of the fact that all clinically significant arrhythmias may be detected using only the ventricular depolarization or QRS signal components, namely QRS duration and R—R interval. In this connection, arrhythmia detection for initiating recording must be distinguished from arrhythmia diagnosis, the latter requiring analysis of all signal components including P and T. All of the P, Q, R, S and T components are recorded for diagnosis on cassette 58 via convertors 50,53 and memory 52 whenever an arrhythmia is detected. According to one important aspect of the present invention, it has been recognized that all clinically significant cardiac events which must be diagnosed by reference to the P and/or T signal components vary sufficiently in QRS duration and/or R—R interval to be detected by the present invention without monitoring the P and T components per se, and thereby eliminating the source of problems inherent in prior art systems that attempt to detect P and T components directly. Thus, the present invention not only simplifies detection techniques but also improves reliability problems inherent in prior art techniques which attempt to detect arrhythmias by, in effect, diagnosing various arrhythmia types.

In accordance with another important feature of the invention, it has been recognized that it is not so much the absolute value of the duration of or interval between QRS signals for a particular patient that is important as measured against fixed standards, as is the relative duration or interval for the particular patient as compared to what is "normal" for him. Indeed, a patient who has suffered heart damage may have a "normal" QRS duration and R—R interval which departs significantly from the above-noted times for a nominally healthy person. Comparison of a patient's QRS duration and R—R interval in the present invention to corresponding running average measurements effectively provides arrhythmia detection for each individual patient by comparing each cardiac event to what is "normal" for him.

Although it may be desirable to measure the actual duration of the QRS signal from the beginning of the Q component, it is convenient and presently preferred to begin measurement at the "peak" of the Q signal utilizing a differentiated signal and conventional zero crossing detection circuitry. As noted above, it is not the absolute duration of the QRS signal that is important but comparison of each duration to past durations. Thus, the first half of the Q component may be ignored so long as QRS duration begins and ends in the same manner for each successive rhythm signal. Similarly, R—R interval may be measured even when there is no discernable R signal component so long as measurement takes place in a similar manner for each successive rhythm signal. In some cases, "R—R interval" may in fact be an S—S interval, for example.

Figure 3:
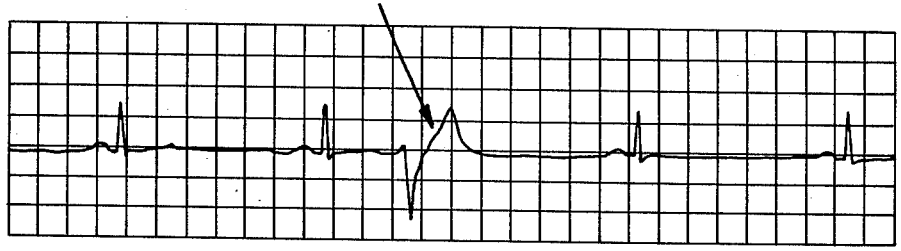

The use of a running average for comparison of QRS duration and R—R interval has the advantage of tracking relatively slow changes in cardiac rhythm associated with changes in patient activities without giving false alarm indications. The invention is designed to be particularly sensitive to perhaps the most dangerous of all arrhythmia types, particularly in ambulatory patients, the premature ventricular contraction or PVC. FIG. 3 illustrates a normal sinus rhythm at a relatively slow rate of fifty-four beats per minute interrupted by a single PVC 62. It is a characteristic of common PVCs that it takes place with a shorter-than-average R—R interval followed by a longer R—R interval called a compensatory pause. The use of three R—R intervals in accordance with a preferred embodiment of the invention, in combination with incorporation of the PVC R—R interval into the running average, insures that the PVC will be detected either at the shortened R—R interval preceding the PVC or at the longer compensatory pause. For example, it is possible that the R—R interval preceding the PVC will only be 25% less than average and, thus, would not trigger recording. However, that shortened R—R interval is then incorporated into the running average so that the succeeding compensatory pause will be substantially greater than 30% of average and recording will be triggered. The use of four intervals for average computation purposes would render the detection circuitry less sensitive, while two intervals would render the circuitry overly sensitive. For these reasons, three R—R intervals in computation of the running average, in combination with a ±30% deviation for detection purposes and incorporation of each rhythm signal whether normal or arrhythmic, into the average, is preferred.

The use of three QRS durations for computation of a running average duration is preferred because the QRS duration circuitry thereby monitors the same portion of the continuing rhythm signal as does the R—R interval circuitry. It will also be noted, that, for normal sinus rhythms of 60 beats per minute or greater, at least three R—R intervals and three QRS durations preceding the detected arrhythmia will be recorded in the preferred embodiment of the invention wherein shift register 52 effectively delays the rhythm signals for three seconds.

An allowable range of plus 20% of QRS duration is recognized in the art as a convenient cut-off for detection of pathological events, particularly PVCs. Thus, PVC 62 in FIG. 3 will be detected both because the QRS duration of the PVC is more than 20% above normal, and the compensatory pause following the PVC is more than 30% above the PVC-modified running average R—R interval. Minus 20% in QRS duration permits the preferred embodiment of the invention to detect unanswered pacemaker spikes, as will be discussed in connection with FIG. 9.

Figure 4:
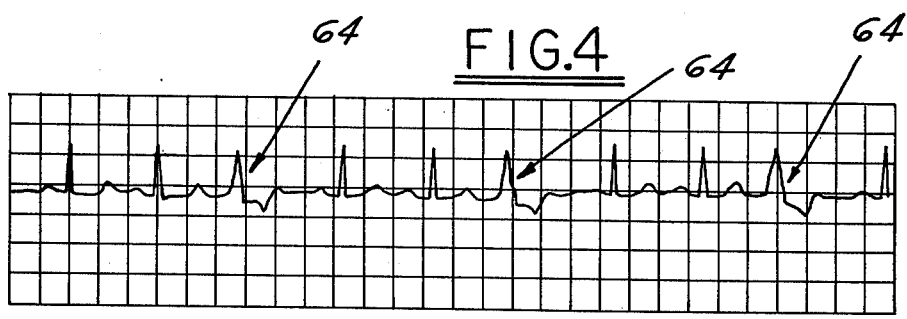

Additional functional features of the invention may be further appreciated with reference to FIGS. 4-9 which illustrates various "typical" pathological events, all of which may be detected and recorded by the preferred embodiment of the invention illustrated in FIG. 1. Each set of cardiac rhythm signals in FIGS. 3-9 is six seconds in duration and is drawn to scale. FIG. 4 illustrates an electrocardiographic abnormality comprising frequent unifocal premature ventricular contractions with a configuration of so-called "ventricular trigeminy". The normal R—R interval in this cardiac rhythm is 600 milliseconds, while the premature R—R interval is 500 milliseconds. Thus, comparator 46 is not activated. However, the QRS duration of the premature ventricular contractions at 64 is 120 milliseconds, which is substantially greater than 120 percent of the normal QRS duration fifty milliseconds. Additionally, the compensatory pause is 740 milliseconds in duration, which is greater than 130% of the PVC-modified R—R interval running average. Thus, OR gate 42 is activated by comparator 40 and comparator 46.

Figure 5:
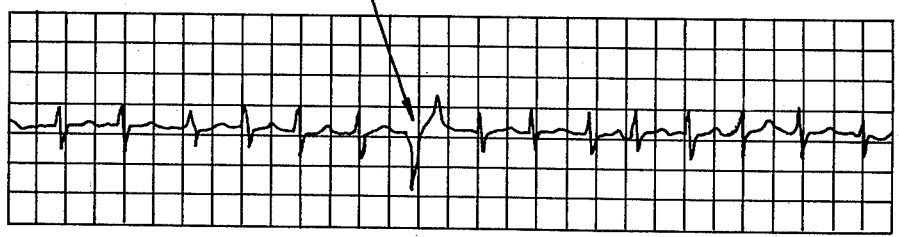

FIG. 5 illustrates a cardiac rhythm abnormality called "atrial fibrillation". In this relatively common abnormality, the patient's atrial activity indicated by the P signal components are chaotic and difficult to discern. The R—R intervals are constantly changing in the illustrated ventricular rhythm from 155 to 170 beats per minute, with an average of about 160 beats per minute. Although the R—R intervals are irregular, they do not depart from the average by plus or minus thirty percent and therefore do not indicate an alarm condition. Thus, the present invention may be used in a patient with atrial fibrillation but reasonably consistent ventricular response without constantly indicating an alarm condition. A premature ventricular contraction as illustrated at 66 in FIG. 5 having a duration of 120 milliseconds, as compared with a seventy millisecond average QRS duration, provides an alarm signal through comparator 40 and gate 42.

Figure 6:

FIG. 6 illustrates a pattern of normal sinus rhythm interrupted by frequent premature atrial contractions 68. The QRS duration of the premature atrial contractions are usually well within normal and relatively constant. However, each premature atrial contraction occurs in the range of forty to two hundred forty milliseconds after the preceding signal complex, which is substantially less than the running average 760 milliseconds R—R interval. Each premature atrial contraction, therefore, activates comparator 46.

Figure 7:
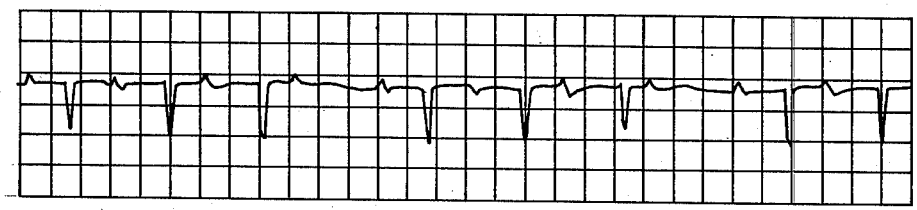
Figure 8:
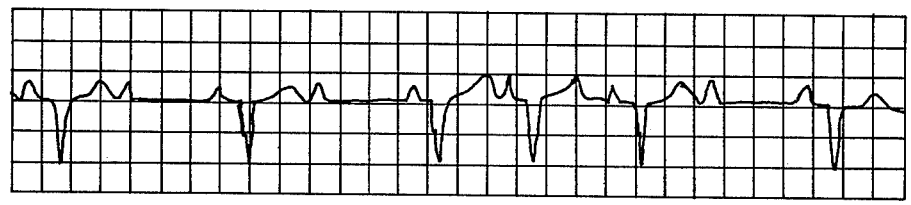

FIGS. 7 and 8 illustrate examples of second degree heart blockage in which the ventricular cardiac muscle responds inconsistently to electrical atrial activity, which is to say that each P wave is not followed by a QRS complex. In second degree heart blockage of the Wenckebach variety illustrated in FIG. 7, the P-R intervals progressively increase until a QRS complex is dropped or "blocked", whereupon the P-R interval again shortens. FIG. 7 illustrates a four-to-three block, i.e., one wherein four P wave components result in only three QRS complexes. The QRS complexes are not distinguished by abnormally prolonged duration, but the rate change is significant in that the R—R interval containing the missed QRS complex is almost twice as long as the average preceding intervals. Thus as illustrated in FIGS. 6 and 7 combined, the present invention is adapted to be responsive both to short and long R—R intervals indicative, respectively, of premature and blocked heart rhythms. FIG. 7 also illustrates the aforementioned feature of the invention whereby a clinically significant arrhythmia diagnostically related to the P singal component is detected, and recorded for later diagnosis, without attempting to monitor the low voltage and frequency P component per se. It will also be recognized that the present invention is adapted to respond to Q, R and S signals of "normal" polarity, as well as complexes of opposite polarity of the type illustrated in FIG. 7.

FIG. 8 illustrates a two-to-one second degree heart block with a period in mid-strip which displays a one-to-one response. Since the patient's normal rhythm displays a two-to-one heart block, the brief one-to-one response is, in fact, double the patient's average rate and an alarm signal is generated.

Figure 9:
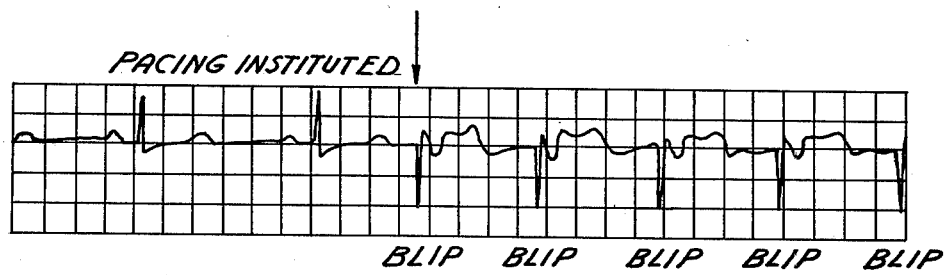

FIG. 9 displays a commonly encountered problem with a patient wearing an intermittently functioning or demand-type electronic pacemaker. The QRS duration following a pacemaker "blip" is normally prolonged because of the position of the pacemaker at the tip of the right ventricle. The pacemaker spike, when first activated, provokes a prolonged QRS duration at the onset of pacing, therefore generating an alarm condition and recording the three-second interval preceding pacing and the first three seconds after the onset of pacing. Similarly, absence of the pacemaker spike following turnoff or failure of the pacemaker, or failure of a pacemaker spike to provoke a subsequent QRS results in a sensed short QRS duration which would result in an alarm signal and recording event. Filter 28 (FIG. 1) passes the high frequency pacemaker spike to the arrhythmia detector circuitry. Where use with a pacemaker is not contemplated, high pass filter 28 may conveniently be replaced by a band pass filter to block both the low frequency P and T signal components and high frequency noise.

Figure 10:
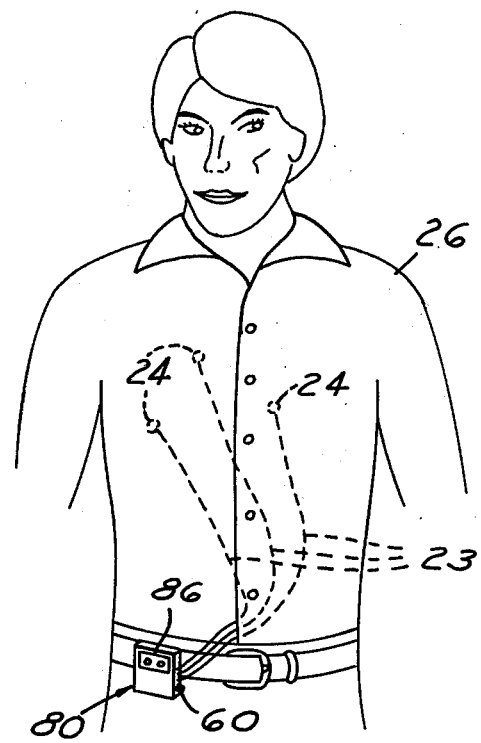
FIG. 10 is a pictorial illustration of a portable version of the invention worn by an ambulatory patient.

Counters 32,34, averagers 38,44, comparators 40,46, gate 42, tape drive 48 and memories 52,54 may be provided in the form of conventional low-cost digital integrated circuitry, while the remainder, including amplifiers 22,30, filter 28 and converters 50,53,55 may be provided in whole or in part by readily available integrated linear circuit components. Indeed, miniature cassette recorders which include both tape drive circuitry 48 and recording circuitry 56 are commercially available. The integrated circuit components and the tape drive and recording head may be readily provided in a compact and rugged portable to be worn by a cardiac outpatient as in the shirt pocket or on his belt as illustrated at 80 in FIG. 10. Portable monitor 80 comprises a case 82 of molded plastic or the like having a suitable clip (not shown) for belt-attachment. Jacks 84 (FIG. 11), such as 3.5 mm connectors, are provided in a side wall of case 82 for connecting the electrode leads 23 to internal circuitry 20. The front cover of case 82 includes a latching window 86 (FIG. 10) for observation and removal of cassette tape 58.

Figure 11:
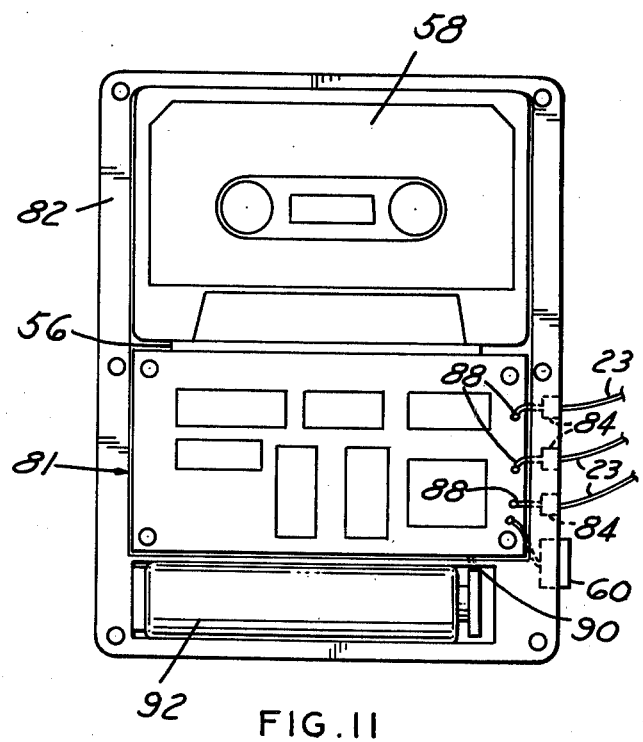
FIG. 11 is an enlarged front elevational view of the portable apparatus in FIG. 10 with front cover removed.

FIG. 11 illustrates portable monitor 80 with the front cover removed. Electronic circuitry 20 (FIG. 1) is embodied in a printed circuit board assembly 81 mounted internally of case 82. Circuit assembly 81 is connected by suitable leads (not shown) to recording head 58, by leads 88 to jacks 84 and by leads 90 to a battery 92, such as a nine volt transistor battery. In accordance with an important feature of the invention, intermittent recording only in response to arrhythmia detection provides extended battery life as compared with continuously recording portable units of the prior art. Additionally, digital shift register memory 52 provides the required continuous signal delaying function with little power drain, particularly as compared with apparatus embodying continuously operative closed loop magnetic tape recording as in U.S. Pat. No. 3,759,248. It will also be appreciated that the recording fidelity and speed, typically on the order of one-eighth inch per second, of a conventional cassette recorder inherently performs a smoothing function between the channel input and the corresponding recording head, thereby eliminating any requirement for demodulation circuitry between the sampled output of memory 52 and the channel input.

It will also be recognized that the arrhythmia detection circuitry provided by the invention and previously described is responsive to the derivative of the cardiac rhythm signal and is therefore substantially independent of the amplitudes of the signal components. Thus, the signal-to-noise ratio is substantially enhanced as compared with prior art monitoring techniques which are responsive in whole or in part to signal amplitude.

It will be appreciated that the present invention offers particular advantages when utilized in a portable battery operated unit since it is maintained in a non-recording state until an arrhythmia is detected, at which time recording begins but continues only for a short duration bracketing the detected arrhythmia. The recorder then returns to non-recording conditions until the next detected arrhythmia. This minimizes battering drain and, very importantly, allows monitoring over long intervals, greater than 24 hours, since the amount of tape used depends only upon the number and frequency of detected arrhythmias. These highly desirable attributes are optimized by the present invention because, as previously described, the present invention is based in large part on the recognition that clinically significant arrhythmias can be detected using QRS components (only), namely QRS duration and R—R interval, based on a differentiated waveform, with preselected ranges of permissable deviations from a running average standard, in order to separate important abnormal events. However, according to the present invention, QRS duration and R-to-R interval are preferably, if not necessarily, detected from this differentiated waveform for example, in the case of QRS interval detection using techniques of the type disclosed in U.S. Pat. Nos. 3,552,386, 3,598,110, 3,616,791 and 3,903,873.

Although the present invention is particularly well adapted for use in a compact and portable cardiac monitoring units, the principles thereof, particularly the arrhythmia detection circuitry embodied in filter 28 to OR gate 42, may readily be incorporated into full scale hospital coronary care units. The invention is intended to embrace the above-noted and all other alternatives, modifications and variations as fall within the spirit and broad scope of the appended claims.

The invention claimed is:

1. Portable apparatus for detecting and recording arrhythmia in cardiac rhythm signals of ambulatory patients comprising a battery, electrode means adapted for placement on a said ambulatory patient for developing electrical signals indicative of said cardiac rhythm signals, first means powered by said battery and responsive exclusively to portions of said electrical signals normally indicative of ventricular depolarization and independent of other portions of said electrical signals for detecting cardiac arrhythmia, said first means comprising second means responsive exclusively to time duration of said portions of said electrical signals normally indicative of ventricular depolarization for generating a first control signal and third means responsive exclusively to time intervals between said ventricular depolarization portions of said electrical signals for generating a second control signal, said first means including said second means and said third means being responsive exclusively to temporal characteristics of said portions of said electrical signals normally indicative of ventricular depolarization and being independent of amplitude of said electrical signals, fourth means responsive to occurrence of either said first or said second control signal for generating an alarm signal of predetermined time duration, a magnetic tape cassette recorder powered by said battery and responsive to said alarm signal for recording both said ventricular depolarization portions and said other portions of said electrical signals for a limited time corresponding to said predetermined time duration and bracketing arrhythmia detected by said first means, such that said recorder is operative to record said signals and drain battery power when arrhythmia are detected and is normally otherwise inoperative, and housing means adapted to be portably worn by a said ambulatory patient and enclosing said battery, said first means, said fourth means and said recorder.

2. The recorder set forth in claim 1 wherein said second means comprises means responsive to comparison of the time duration of each said ventricular depolarization signal portion with a running average duration of a preselected number of immediately preceding ventricular depolarization signal portions, wherein said third means comprises means responsive to comparison of the time interval between each said ventricular depolarization signal portion and the immediately preceding ventricular depolarization signal portion with a running average of intervals between the same said preselected number of immediately preceding ventricular depolarization signal portions, such that said second means and said third means compare temporal characteristics of each said ventricular depolarization signal portion to the temporal characteristics of the same said preceding ventricular depolarization signal portions, and wherein said predetermined time duration is such that electrical signals which include said predetermined number of said preceding ventricular depolarization signal portions are recorded together with a said arrhythmia, such that each detected arrhythmia is recorded together with the same said preceding ventricular depolarization signal portions with which said detected arrhythmia was compared in said first means and said second means.

3. The recorder set forth in claim 2 wherein said predetermined number is three and wherein said predetermined time duration is six seconds.

4. The portable apparatus set forth in claim 1, 2 or 3 further comprising means adapted to be manually operable by a wearer of said apparatus for activating said recorder independently of said fourth means.

5. The portable apparatus set forth in claim 4 wherein said recorder comprises a multiple-channel cassette recorder, said electrical signals being recorded on one channel of said recorder, said apparatus further comprising means for recording on other channels of said recorder data indicative of time of day when said recorder is activated and whether said recorder has been activated by said fourth means or by said manually operable means.

6. The portable apparatus set forth in claim 2 wherein said second means is responsive to deviation of ±20% of said running average duration of three preceding ventricular depolarization signal portions, and wherein said third means is responsive to ±30% of said running average interval between three preceding ventricular depolarization signal portions.

7. A method of detecting and recording cardiac arrhythmia in an ambulatory patient comprising the steps of:
(a) continuously monitoring the surface EKG signals of an ambulatory patient,
(b) detecting cardiac arrhythmia responsive exclusively to time durations of and time intervals between successive portions of said EKG signals indicative of ventricular depolarization and independently of both other portions of said EKG signals and amplitude of said ventricular depolarization portions of said successive signals, and
(c) intermittently recording the entirety of said EKG signals monitored in said step (a) when an arrhythmia is detected in said step (b) for a limited time bracketing arrhythmia detected in said step (b).

* * * * *